United States Patent
Wu et al.

(10) Patent No.: US 10,080,580 B2
(45) Date of Patent: Sep. 25, 2018

(54) CURETTE FOR PITUITARY ADENOMA SURGERY

(71) Applicants: Hsing-Fu Wu, Changhua (TW);
Tsair-Rong Chen, Changhua (TW);
Yu-Lin Juan, Changhua (TW)

(72) Inventors: Hsing-Fu Wu, Changhua (TW);
Tsair-Rong Chen, Changhua (TW);
Yu-Lin Juan, Changhua (TW)

(73) Assignees: Ying Changs Industry Corp.,
Chunghua (TW); **Dept. of Electrical
Engineering National Changhua
University of Education**

( * ) Notice: Subject to any disclaimer, the term of this patent is extended or adjusted under 35 U.S.C. 154(b) by 245 days.

(21) Appl. No.: 14/964,372

(22) Filed: Dec. 9, 2015

(65) Prior Publication Data

US 2017/0164975 A1    Jun. 15, 2017

(51) Int. Cl.
*A61B 17/32* (2006.01)
*A61B 17/3207* (2006.01)
*A61B 90/00* (2016.01)
*A61B 17/00* (2006.01)

(52) U.S. Cl.
CPC ............... *A61B 17/320708* (2013.01); *A61B 2017/00238* (2013.01); *A61B 2090/034* (2016.02)

(58) Field of Classification Search
CPC ............ A61B 17/320708; A61B 2017/320741
See application file for complete search history.

(56) References Cited

U.S. PATENT DOCUMENTS 4,627,444 A * 12/1986 Brooker ............. A61B 10/0045
600/571
6,328,749 B1 * 12/2001 Kalmann ......... A61B 17/00008
606/159

\* cited by examiner

*Primary Examiner* — Kathleen Holwerda
*Assistant Examiner* — Christina Lauer
(74) *Attorney, Agent, or Firm* — Che-Yang Chen; Law Offices of Scott Warmuth

(57) ABSTRACT

A curette for pituitary adenoma surgery may include a curette having a tubular blade portion. A first cutting edge is formed at a first end of the blade portion, and a protective shell is formed at an outer periphery of the first cutting edge. A first annular ring formed at a first end of the protective shell is located at the same side of the first cutting edge, and a rod portion extended from a surface of the protective shell is configured to provide a handhold for a user. The first annular ring of the protective shell can prevent the first cutting edge of the blade portion from accidentally cutting the meninges or blood vessels during pituitary adenoma surgery. Thus, the curette can improve the efficiency of the surgery and lower surgery time, anesthetic dosage and risk of the surgery.

4 Claims, 4 Drawing Sheets

CURETTE FOR PITUITARY ADENOMA SURGERY

FIELD OF THE INVENTION

The present invention relates to a curette for pituitary adenoma surgery, and more particularly to a curette to provide an improved protective effect for meninges and blood vessels during the pituitary adenoma surgery.

BACKGROUND OF THE INVENTION

Nowadays, there are numerous treatments for pituitary adenoma, including medical management, radiation therapy, or surgery, and the pituitary adenoma surgery is a typical choice of the treatment. Pituitary adenomas are usually benign tumors, and the patient can be fully recovered after the tumors are removed. Generally, the conventional curette (30) comprises a tubular blade portion (31) formed at a first end thereof, and an opening formed at a first end of the blade portion (31) has an oblique cutting edge (32). When the curette (30) is used in pituitary adenoma surgery, the blade portion (31) of the curette (30) is inserted from the nose to reach the pituitary gland of patient, and the tumors are able to be removed by the cutting edge (32) of the blade portion (31).

However, the conventional curette is disadvantageous because: (i) during the surgery, the blade portion (31) of the curette (30) is inevitably to touch the meninges and blood vessels of a patient, leading to doctor having to pay much attention during surgery. As a result, the surgery time and anesthetic dosage are increase, and also the recovery rate of the patient is reduced. Moreover, it will cause patient with massive hemorrhage when the blade portion (31) accidentally cuts the meninges or blood vessels during surgery, resulting in increasing the risk of surgery; (ii) Since the conventional curette (30) usually comprises only one cutting edge (32) formed at the first end of blade portion (31), the blade portion (31) has to be rotated to change the cutting angle of the blade portion (31) during surgery, resulting in lowering the efficiency of surgery; and (iii) when the blade portion (31) of the curette (30) has two cutting edges (32) respectively formed at two ends of the of blade portion (31), doctor has to pay much attention to prevent the cutting edges (32) from hurting the meninges or blood vessels of patient during surgery, leading to increasing the risk and time of surgery. Therefore, there remains a need for a new and improved design for a curette for pituitary adenoma surgery to overcome the problems presented above.

SUMMARY OF THE INVENTION

The present invention provides a curette for pituitary adenoma surgery, which comprises a curette having a tubular blade portion. A first cutting edge is formed at a first end of the blade portion, and a protective shell is formed at an outer periphery of the first cutting edge. Also, an annular recessed portion is located between the first cutting edge and the protective shell, and a dimension of the annular recessed portion is gradually narrow from the first cutting edge to the protective shell to form into a tapered shape, leading to increasing the sharpness of the first cutting edge. A first annular ring formed at a first end of the protective shell is located at the same side of the first cutting edge, and a rod portion extended from a surface of the protective shell is configured to provide a handhold for a user. A second cutting edge is formed at a second end of the blade portion, and a second annular ring formed at a second end of the protective shell is located at the same side of the second cutting edge. Furthermore, positions of surfaces of the first annular ring and the second annular ring are respectively outer than surfaces of the first cutting edge and the second cutting edge.

Comparing with conventional curette, the present invention is advantageous because: (i) since the curette has the protective shell formed at the outer periphery of the blade portion, and the first annular ring and the second annular ring are respectively formed at the two ends of the protective shell, the curette is able to improve the recovery rate of the patient and the efficiency of the surgery. Also, the curette and is able to lower the surgery time, anesthetic dosage and the risk of the surgery, and is able to prevent patients from massive hemorrhage causing by the blade portion accidentally cutting the meninges or blood vessels during surgery; (ii) the curette of the present invention comprises two cutting edges, leading to improve the efficiency of the surgery; and (iii) since the positions of the surfaces of the first annular ring and the second annular ring are respectively outer than the surfaces of the first cutting edge and the second cutting edge, the curette is able to efficiently provide the protective effect for meninges and blood vessels during the pituitary adenoma surgery.

DETAILED DESCRIPTION OF THE INVENTION

The detailed description set forth below is intended as a description of the presently exemplary device provided in accordance with aspects of the present invention and is not intended to represent the only forms in which the present invention may be prepared or utilized. It is to be understood, rather, that the same or equivalent functions and components may be accomplished by different embodiments that are also intended to be encompassed within the spirit and scope of the invention.

Unless defined otherwise, all technical and scientific terms used herein have the same meaning as commonly understood to one of ordinary skill in the art to which this invention belongs. Although any methods, devices and materials similar or equivalent to those described can be used in the practice or testing of the invention, the exemplary methods, devices and materials are now described.

All publications mentioned are incorporated by reference for the purpose of describing and disclosing, for example, the designs and methodologies that are described in the publications that might be used in connection with the presently described invention. The publications listed or discussed above, below and throughout the text are provided solely for their disclosure prior to the filing date of the present application. Nothing herein is to be construed as an admission that the inventors are not entitled to antedate such disclosure by virtue of prior invention.

Figure 1:
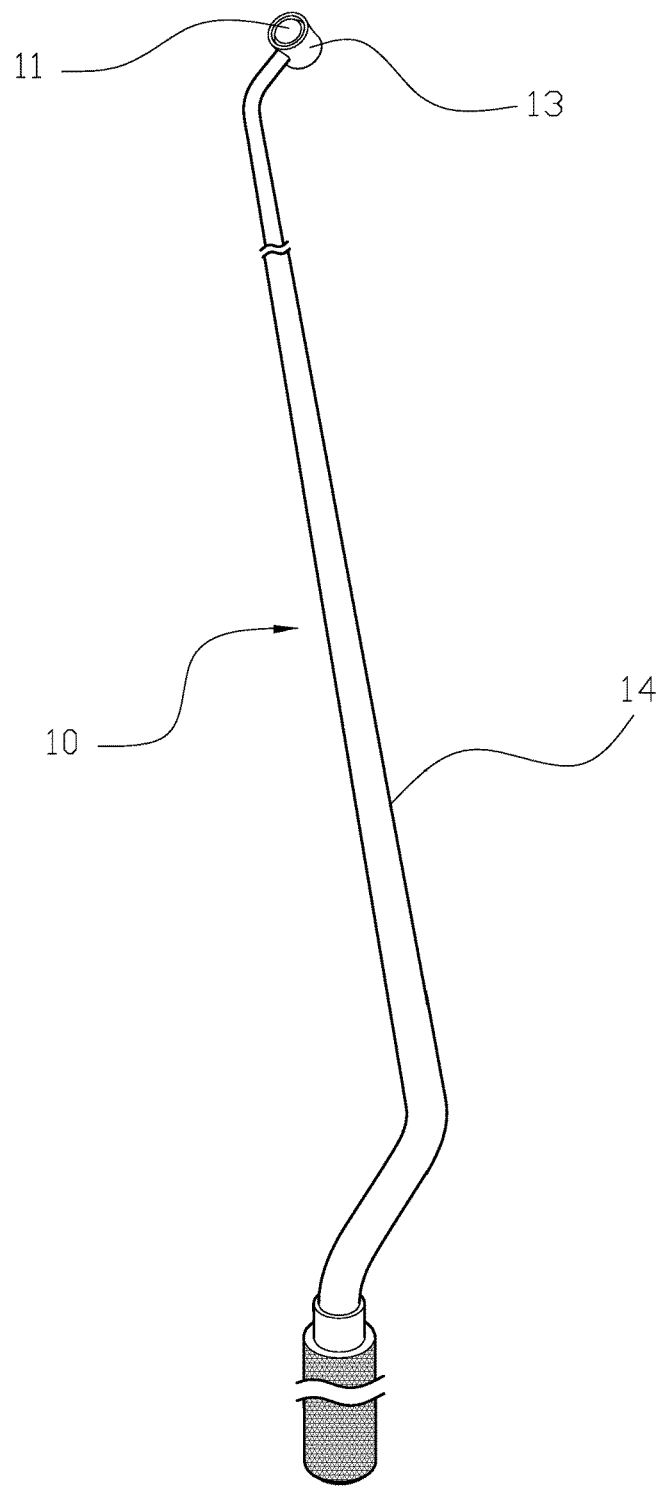
FIG. 1 is a three-dimensional view of the curette of the present invention.
Figure 2:
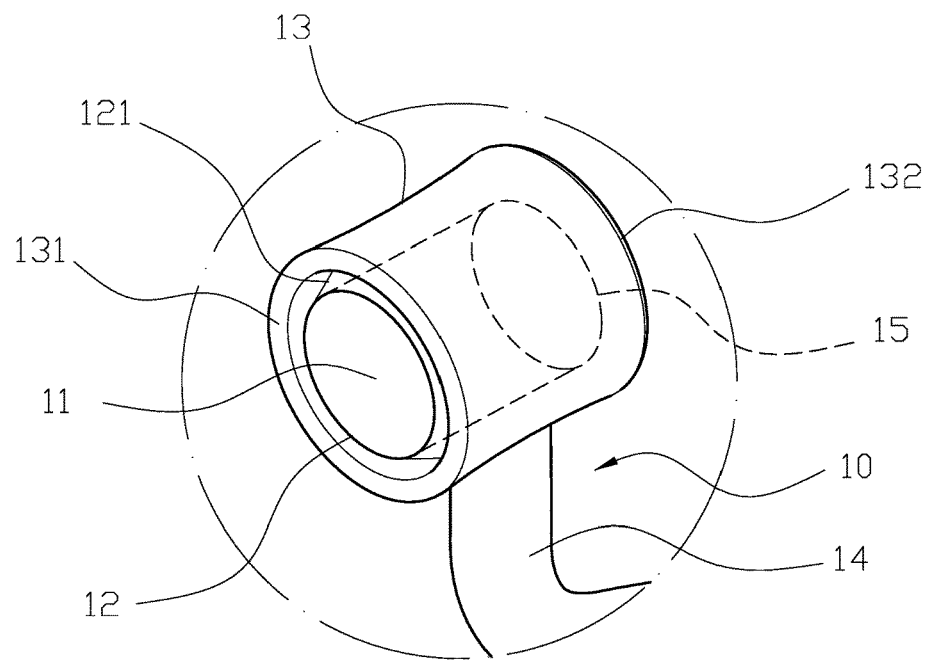
FIG. 2 is a partially enlarged, three-dimensional view of the blade portion of the curette in the present invention.
Figure 3:
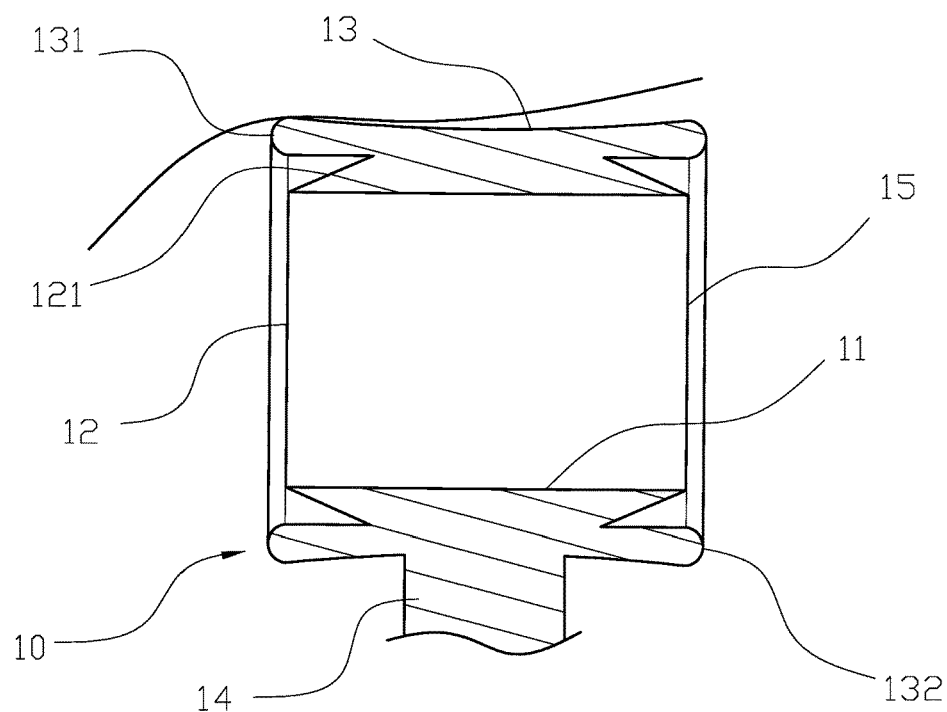
FIG. 3 is a sectional view of the blade portion of the curette in the present invention.
Figure 4:
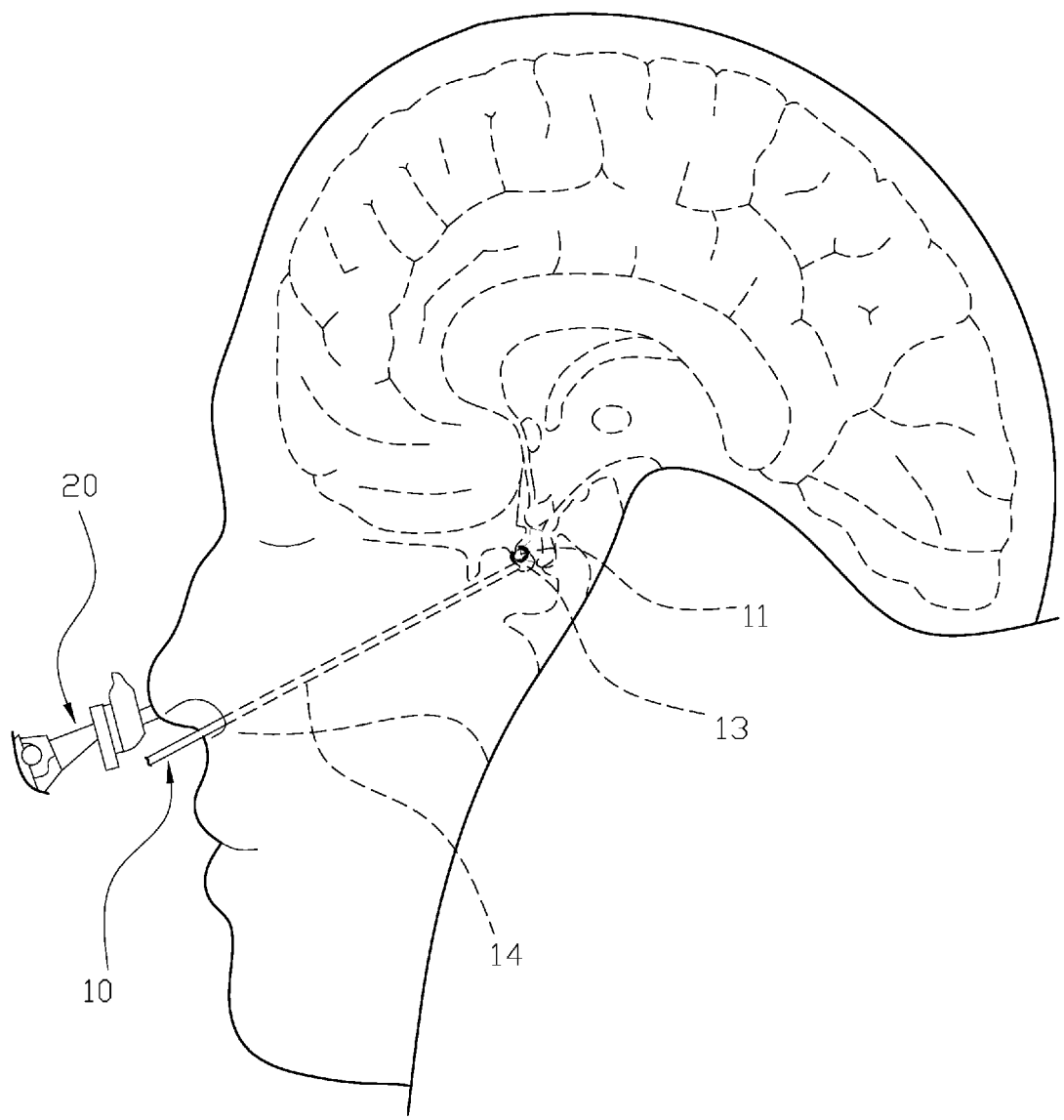
FIG. 4 is a schematic view of the curette of the present invention when in use.
Figure 5:
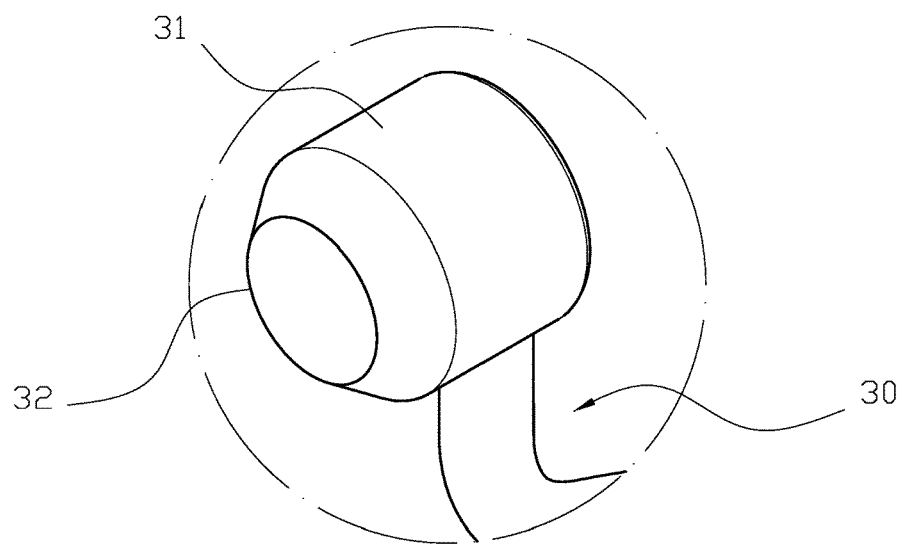
FIG. 5 is a prior art.
Figure 6:
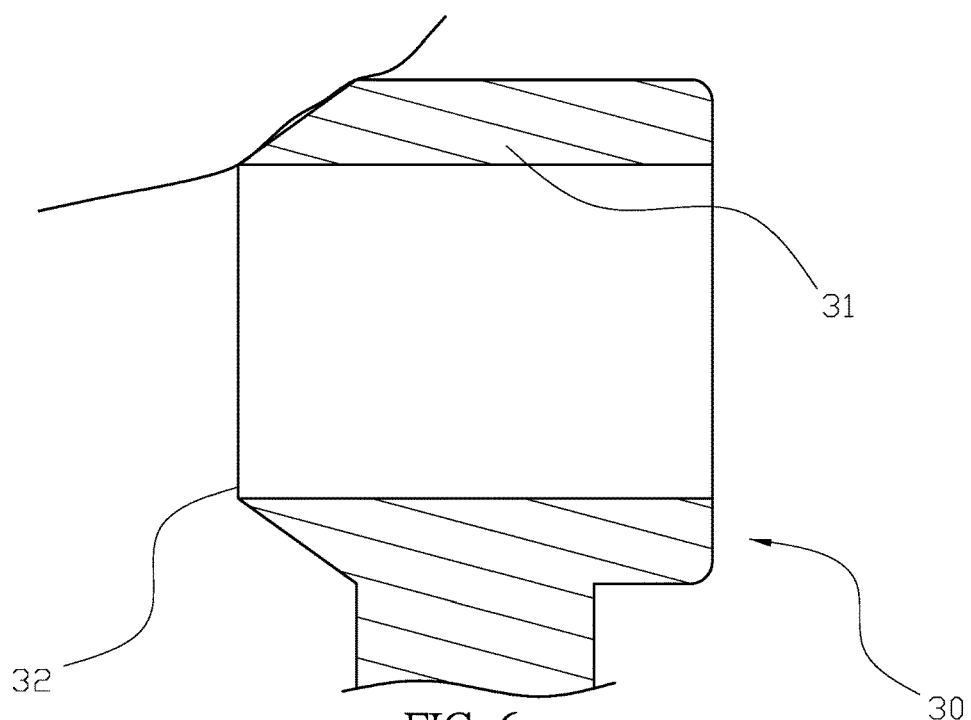
FIG. 6 is a prior art.

In order to further understand the goal, characteristics and effect of the present invention, a number of embodiments along with the drawings are illustrated as following:

Referring to FIGS. 1 to 3, the present invention provides a curette for pituitary adenoma surgery, which comprises a curette (10) having a tubular blade portion (11). A first cutting edge (12) is formed at a first end of the blade portion (11), and a protective shell (13) is formed at an outer periphery of the first cutting edge (12). Also, an annular recessed portion (121) is located between the first cutting edge (12) and the protective shell (13), and a dimension of the annular recessed portion (121) is gradually narrow from the first cutting edge (12) to the protective shell (13) to form into a tapered shape, leading to increasing the sharpness of the first cutting edge (12). Further, because of the cooperation between the protective shell (13) and the annular recessed portion (121), the cutting area of the curette (30) is increased. A first annular ring (131) formed at a first end of the protective shell (13) is located at the same side of the first cutting edge (12), and a rod portion (14) extended from a surface of the protective shell (13) is configured to provide a handhold for a user. A second cutting edge (15) is formed at a second end of the blade portion (11), and a second annular ring (132) formed at a second end of the protective shell (13) is located at the same side of the second cutting edge (15). Thus, the curette (10) comprises two cutting edges (12)(15) on the blade portion (11), leading to increasing the efficiency of pituitary adenoma surgery. Furthermore, since positions of surfaces of the first annular ring (131) and the second annular ring (132) are respectively outer than surfaces of the first cutting edge (12) and the second cutting edge (15), the first annular ring (131) and the second annular ring (132), which are formed on the protective shell (13), are able to prevent the cutting edges (12)(15) from hurting the meninges or blood vessels of patient during surgery. As a result, the curette (10) is able to efficiently reduce the surgery time and anesthetic dosage, and is able to lower the risk of the surgery.

When in use, referring to FIGS. 1 to 4, a first end of the rod portion (14) of the curette (10) comprises the blade portion (11), and a length of the rod portion (14) allows the blade portion (31), which is inserted from one nostril, to reach the pituitary gland of patient. Moreover, an endoscopy (20) inserted from the other nostril is configured to monitor positions of the tumors and the blade portion (11), leading to efficiently cutting tumors by the first cutting edge (12) and the second cutting edge (15). As a result, the curette (10) is able to improve the recovery rate of the patient, and prevent patients from massive hemorrhage causing by the blade portion (11) accidentally cutting the meninges or blood vessels during surgery.

Comparing with conventional curette, the present invention is advantageous because: (i) since the curette (10) has the protective shell (13) formed at the outer periphery of the blade portion (11), and the first annular ring (131) and the second annular ring (132) are respectively formed at the two ends of the protective shell (13), the curette (10) is able to improve the recovery rate of the patient and the efficiency of the surgery. Also, the curette (10) and is able to lower the surgery time, anesthetic dosage and the risk of the surgery, and is able to prevent patients from massive hemorrhage causing by the blade portion accidentally cutting the meninges or blood vessels during surgery; (ii) the curette (10) of the present invention comprises two cutting edges (11)(15), leading to improve the efficiency of the surgery; and (iii) since the positions of the surfaces of the first annular ring (131) and the second annular ring (132) are respectively outer than the surfaces of the first cutting edge (12) and the second cutting edge (15), the curette (10) is able to efficiently provide the protective effect for meninges and blood vessels during the pituitary adenoma surgery.

Having described the invention by the description and illustrations above, it should be understood that these are exemplary of the invention and are not to be considered as limiting. Accordingly, the invention is not to be considered as limited by the foregoing description, but includes any equivalents.

What is claimed is:

1. A curette for pituitary adenoma surgery comprising: a tubular blade portion comprising a first cutting edge and a second cutting edge; wherein the first cutting edge is formed at a first end of the tubular blade portion and the second cutting edge is formed at a second end of the tubular blade portion, opposite the first cutting edge; a protective shell formed at an outer periphery of the first cutting edge and the second cutting edge, the protective shell comprising a first annular ring formed at a first end of the protective shell, located at the same side of the curette as the first end of the tubular blade portion and a second annular ring formed at a second end of the protective shell, located at the same side of the curette as the second end of the tubular blade portion; wherein the first and second annular rings of the protective shell are configured to prevent cutting of the meninges or blood vessels during pituitary adenoma surgery; and a rod portion extended from a surface of the protective shell, the rod portion configured to provide a handhold for a user.

2. The curette for pituitary adenoma surgery of claim 1, wherein an annular recessed portion is located between the first cutting edge and the protective shell, and a dimension of the annular recessed portion is gradually narrow from the first cutting edge to the protective shell to form into a tapered shape, leading to increasing the sharpness of the first cutting edge.

3. The curette for pituitary adenoma surgery of claim 1, wherein a surface of the first cutting edge shrinks into a surface formed by the first annular ring.

4. The curette for pituitary adenoma surgery of claim 1, wherein a surface of the second cutting edge shrinks into a surface formed by the second annular ring.

* * * * *